US006979449B1

(12) United States Patent
Mock

(10) Patent No.: US 6,979,449 B1
(45) Date of Patent: Dec. 27, 2005

(54) **ACELLULAR IMMUNOGENIC COMPOSITIONS AND ACELLULAR VACCINE COMPOSITIONS AGAINST *BACILLUS ANTHRACIS***

(75) Inventor: Michèle Mock, Paris (FR)

(73) Assignees: Institut Pasteur, Paris (FR); Centre National de la Recherche Scientifique-CNRS, Paris (FR)

( * ) Notice: Subject to any disclaimer, the term of this patent is extended or adjusted under 35 U.S.C. 154(b) by 0 days.

(21) Appl. No.: 10/069,961

(22) PCT Filed: Sep. 8, 2000

(86) PCT No.: PCT/FR00/02494

§ 371 (c)(1),
(2), (4) Date: Jul. 19, 2002

(87) PCT Pub. No.: WO01/19395

PCT Pub. Date: Mar. 22, 2001

(30) Foreign Application Priority Data

Sep. 10, 1999 (FR) .................................. 99 11384

(51) Int. Cl.[7] ............................................. A61K 39/07

(52) U.S. Cl. .............................. 424/246.1; 424/234.1; 424/236.1; 424/235.1; 424/193.1; 424/197.11; 424/200.1; 530/350; 435/242; 435/252.3; 435/252.31

(58) Field of Search .......................... 434/234.1, 246.1, 434/236.1, 235.1, 193.1, 197.11, 200.1; 530/350; 435/242, 252.3, 252.31

(56) References Cited

FOREIGN PATENT DOCUMENTS

EP 0 739 981 10/1996

OTHER PUBLICATIONS

Kraevets et al. Microbiol. Res. Instit. Jul. 1998. Derwent abstract only.*
Pezard et al. Infect. Immun. 1995. 63(4): 1369-1372.*
Ivins et al. Infect. Immun. May 1986. 52(2): 454-7.*
Ivins et al. Eur. J. Epidem. Mar. 1988. 4(1): 12-19.*
S.L. Welkos et al.: “Comparative safety and efficacy against *Bacillus anthracis* of protective antigen and live vaccines in mice” Microbial Pathogenesis, vol. 5, No. 3, pp. 127-140 1988.
P.C.B. Turnbull: “ Anthrax vaccines: past, present, and future” Vaccine, vol. 9, No. 8, pp. 533-539 Aug. 1, 1991.
A.V. Stepanov et al.: “Development of novel vaccines against anthrax in man” Journal of Biotechnology, vol. 44, No. 1, pp. 155-160 Jan. 26, 1996.
V.A. Abalakin et al.: “Protective and other biological properties of *Bacillus anthracis* soluble antigen” Journal of Hygiene, Epidemiology, Microbiology, and Immunology, vol. 35, No. 1, pp. 83-91 1991.

* cited by examiner

*Primary Examiner*—Jennifer E. Graser
(74) *Attorney, Agent, or Firm*—Oblon, Spivak, McClelland, Maier & Neustadt, P.C.

(57) ABSTRACT

The invention concerns an acellular immunogenic or vaccine composition for producing antibodies against *Bacillus anthracis* comprising a protective antigen (PA) and killed and optionally purified spores, obtained from mutating strains of *Bacillus anthracis* and their uses.

13 Claims, 3 Drawing Sheets

FIGURE 3

Figure 1:
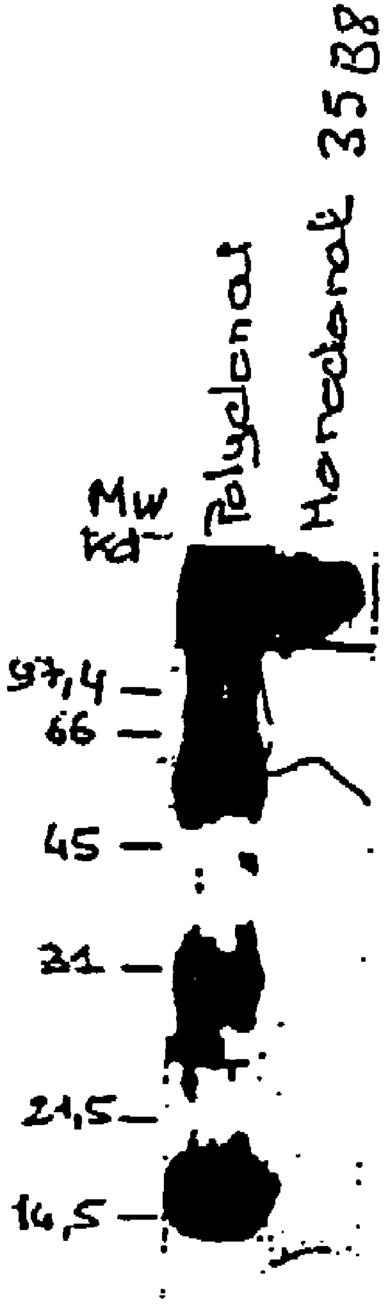

| Strain | Genotype | Resistance to an antibiotic | Factors produced | | | Parental strain |
|---|---|---|---|---|---|---|
| 7702 | pXO1 | Ø | PA | LF | EF | Sterne strain (Pasteur collection) |
| RPA | pXO1-*pag*Δ(1805-2871) | Spc | — | LF | EF | 7702 |
| RPA200 | pXO1-*pag*Δ(1805-4105) | Erm | — | LF | EF | 7702 |
| RPL | pXO1-*lef*Δ(2105-2970) | Spc | PA | — | EF | 7702 |
| RPL200 | pXO1-*lef*Δ(405-2911) | Erm | PA | — | EF | 7702 |
| RPE | pXO1-*cya*Δ(400-2311) | Spc | PA | LF | — | 7702 |
| RPE346 | pXO1-*cya*346/353 | Ø | PA | LF | EF346/353 | RPE |
| RPL686 | pXO1-*lef*686 | Ø | PA | LF686 | EF | RPL |
| RPL686Δ*cya* | pXO1-*cya*Δ(1414-2420) | Kan | PA | LF686 | | RPL686 |
| RPLC2 | pXO1-*lef*686-*cya*346/353 | Ø | PA | LF686 | EF346/353 | RPL686Δ*cya* |
| RPA163 | pXO1-*pag*Δ(2374-2394) | Ø | PA163 | LF | EF | RPA |
| RPA313 | pXO1-*pag*Δ(2826-2933) | Ø | PA313 | LF | EF | RPA |
| RPA705 | pXO1-*pag*Δ(4005-4053) | Ø | PA705 | LF | EF | RPA200 |
| RPA608 | pXO1-*pag*608 | Ø | PA608 | LF | EF | RPA200 |

ACELLULAR IMMUNOGENIC COMPOSITIONS AND ACELLULAR VACCINE COMPOSITIONS AGAINST *BACILLUS ANTHRACIS*

The present invention relates to acellular immunogenic compositions and also to acellular vaccine compositions against *Bacillus anthracis*, and to the uses thereof in human medicine and in veterinary medicine.

*Bacillus anthracis* (*B. anthracis*), the agent responsible for anthrax, or charbon, is an aerobic spore-forming Gram-positive bacterium.

This agent induces an infection either by intradermal inoculation or by ingestion or inhalation of the spores (Klein F. et al., (1966), *J. Infect. Dis.,* 116, 1213–138; Friedlander A. M. et al., (1993), *J. Infect. Dis.* 167, 1239–1242), the transformation of which into vegetative cells, encapsulated and toxinogenic forms, allows the bacterium to proliferate and to synthesize its virulence factors.

The inventors have recently shown, in a murine model of pulmonary infection with *B. anthracis*, that alveolar macrophages are the primary site of the germination, which is rapidly followed by the expression of the toxin genes, confirming that the encounter between the spore and the host is crucial for the pathogenicity of *B. anthracis* (Guidi-Rontani E; et al., *Molecular Biology, (*1999), 31, 9–17).

The main virulence factors are:

- the antiphagocytic capsule consisting of poly-γ-D-glutamic acid (Avakyan A. A. et al. (1965), *J. of Bacteriology,* 90, 1082–1095) and
- three protein factors which act in paired combination. The edematogenic toxin (PA-EF) induces an edema after subcutaneous injection, whereas the lethal toxin (PA-LF) is responsible for animal death after intravenous injection (J. W. Ezzell et al., (1984), *Infect. Immun.,* 45, 761–767). The factor present in both combinations is the protective antigen (PA) which is involved in the binding of toxins to the target cells. The other two factors, the edematogenic factor (EF) and the lethal factor (LF), are responsible for the manifestation of the toxic effect.

The simultaneous production of the capsule and of the of the toxins is essential for the manifestation of the pathogenic power.

The genes encoding the enzymes which synthesize the capsule are carried by the pXO2 plasmid (Green B. D. et al., (1985), *Infect. Immun.,* 49, 291–297; Uchida I. et al., (1985), *J. Gen. Microbiol.,* 131, 363–367) and the three genes pag, cya and lef, which encode, respectively, the PA, EF and LF factors, are carried by the pXO1 plasmid, which was described by Mikesell P. et al. (*Infect. Immun, (*1983), 39, 371–376).

Although many studies have shown that PA is the main antigen responsible for protection in the context of natural immunization or immunization acquired by vaccination, the inventors have shown that LF is also a powerful immunogen (Mock M. *Annales de l'Institut Pasteur* [Annals of the Pasteur Institute] December 1990).

In order to clarify the role of the toxin components in the toxicity of *B. anthracis*, the inventors have constructed various mutants. Thus, they have characterized a strain which lacks the pXO2 plasmid and lacks PA by modification of the pXO1 plasmid. Due to the absence of PA, this strain is no longer lethal in nature (Cataldi A. et al. (1990), *Molecular Microbiology,* 4, 1111–1117).

In order to investigate the elements which may be involved in immunization against infection with *B. anthracis*, the inventors have constructed mutants lacking at least one of the toxicity factors responsible for pathogenicity, i.e. deficient in PA, in EF or in LF, or even lacking the pXO1 plasmid and also lacking the pXO2 plasmid. Although lacking toxicity or exhibiting attenuated toxicity, the single mutants, in particular RP9 (EF-) (Collection Nationale de Cultures et de Microorganismes [National Collection of Cultures and of Microorganisms] held by the Institut Pasteur under the number I-1094, dated May 2, 1991) and RP10 (LF-) (Collection Nationale de Cultures et de Microorganismes held by the Institut Pasteur under the number I-1095, dated May 2, 1991), and the double mutant RP 42 (Collection Nationale de Cultures et de Microorganismes held by the Institut Pasteur under the number I-2271, dated Jul. 28, 1999) proved to be capable of producing antibodies immunoprotective against infection with a wild-type Sterne strain. These mutants are described in international application No. 92/19720, and in the articles by C. Pezard et al., (*Infection and Immunity*, (1991), 59, 3472–3477 and *J. General Microbiology*, (1993), 139, 2459–2463).

Currently, the veterinary vaccine marketed (Mérial®) is a live vaccine composed of a suspension of spores of the Sterne strain of *B. anthracis.* Its protective efficacy in animals varies depending on the batch, without it being possible to determine the causes of these variations.

This random efficacy, side effects and also the potential risk of disseminating live germs in the environment make its use in humans impossible.

In human medicine, two vaccines against anthrax, essentially developed in Great Britain and in the United States, are used. They are acelullar vaccines consisting mainly of the protective antigen (PA), prepared from culture supernatants of the toxinogenic Sterne strain of *B. anthracis*, and of an adjuvant which can be used in human medicine, aluminum hydroxide.

Recent studies on these two vaccines have shown that the British vaccine, containing traces of EP and of LF which induce an antibody response by ELISA, is more efficacious in guinea pigs than the American vaccine, which apparently lacks these two components (Turnbull P. C. et al., (1991), *Vaccine,* 9, 533–539).

However, these two vaccines have a certain number of drawbacks:

- the vaccination protocol is restrictive, since it requires six injections in eighteen months, followed by one booster per year,
- they induce harmful side effects which limit their use,
- the protection induced by these acellular vaccines in animals, against a challenge with a virulent strain, is never complete, unlike that obtained with the live vaccine.

Given the magnitude of the infections caused by *B. anthracis*, many studies are currently dedicated to improving the vaccine so that it does not have the drawbacks set out above, but at the same time exhibits the same protection as the live vaccine.

In this context, the inventors have given themselves the aim of providing a reliable efficacious acellular vaccine free of side effects which overcomes the drawbacks of the existing vaccines and the vaccine properties of which are easy to control.

Consequently, a subject of the present invention is an acellular immunogenic composition capable of inducing an immune response against *B. anthracis* infections, characterized in that it comprises:

a protective antigen (PA), killed, optionally purified, spores obtained either from mutant strains of *B. anthracis* carrying one or more mutations chosen from mutations in at least one gene encoding a protein responsible for a toxic effect, in *B. anthracis*, or from mutant strains of *B. anthracis* lacking at least one of the pXO1 and pXO2 plasmids, combined at least with a pharmaceutically acceptable vehicle.

In an advantageous embodiment of the invention, said acellular immunogenic composition is capable of producing antibodies against *B. anthracis.*

A subject of the present invention is also an acellular vaccine composition against *B. anthracis*, characterized in that it comprises:

a protective antigen (PA), killed, optionally purified, spores obtained either from mutant strains of *B. anthracis* carrying one or more mutations chosen from mutations in at least one gene encoding a protein responsible for a toxic effect, in *B. anthracis*, or from mutant strains of *B. anthracis* lacking at least one of the pXO1 and pXO2 plasmids, combined at least with a pharmaceutically acceptable vehicle and with at least one adjuvant.

For the purpose of the present invention, the term "acellular" means that the immunogenic or vaccine composition no longer contains any viable cells (killed spores).

The adjuvants used are adjuvants conventionally used and will, in particular, be either saponin, in the case of the veterinary vaccine, or advantageously chosen from the group consisting of aluminum hydroxide and squalene, in the case of the human vaccine.

In the context of the present invention, the spores may be killed by any physical or chemical means which leads to their inactivation. By way of example, mention may be made of treatment with formaldehyde or irradiation.

For the purpose of the present invention, the term "mutation" is intended to mean a deletion, modification or addition in the gene concerned, which results in a gene either lacking its ability to produce the corresponding protein or capable of producing an inactive protein.

According to a particular embodiment of the invention, the immunogenic compositions and the vaccine compositions may also comprise at least one detoxified exotoxin chosen in particular from the group consisting of the lethal factor (LF) and the edematogenic factor (EF), which have been detoxified, i.e. which have lost their toxic properties.

These inactivated protein factors may in particular be obtained by expressing the genes which have been mutated in the sequence encoding the active site of said protein factors (cya or lef).

The immunogenic and vaccine compositions according to the invention have, surprisingly, a strong protective capacity, of the order of 100%, which is clearly greater than that obtained with the PA alone or the killed spores alone, which makes it possible to obtain complete immunization with a single injection under the conditions for the veterinary vaccine, and two injections under the conditions for the vaccine for human use.

According to another advantageous embodiment of the immunogenic and vaccine compositions according to the invention, the spores are derived from a strain of *B. anthracis* chosen from the group consisting of the following strains: Sterne 7702 (M. Sterne J. Vet. Sci. Anima. Indust., (1939), 13, 315–317), RPLC2 (Collection Nationale de Cultures et de Microorganismes held by the Institute Pasteur (28 rue du Dr Roux, 75724 Paris Cedex 15, France) under the number I-2270, dated Jul. 28, 1999) and RP42 (Collection Nationale de Cultures et de Microoganismes held by the Institut Pasteur under the number I-2271, dated Jul. 28, 1999).

In another advantageous embodiment of the immunogenic and vaccine compositions according to the invention, the protective antigen is chosen from the group consisting of the purified protective antigens derived from any wild-type or mutated Sterne strain of *B. anthracis*, and the recombinant protective antigens, in particular that produced by *B. subtilis.*

Advantageously, the protective antigen is derived from the RP42 strain (Collection Nationale de Cultures et de Microorganismes held by the Institut Pasteur under the number I-2271, dated Jul. 28, 1999).

The subject of the present invention is also the RPLC2 strain deposited with the Collection Nationale de Cultures et de Microorganismes held at the Institut Pasteur under the number I-2270, dated Jul. 28, 1999).

A subject of the present invention is also the use of at least one antibody directed against the spores derived from strains obtained either from mutant strains of *B. anthracis* carrying one or more mutations chosen from mutations in at least one gene encoding a protein responsible for a toxic effect, in *B. anthracis*, or from mutant strains of *B. anthracis* lacking at least one of the pXO1 and pXO2 plasmids, for producing a medicinal product capable of inducing passive immunization. In fact, antibiotics are the only current treatment against anthrax and must be administered early, before the appearance of the toxic shock. Consequently, a serotherapy aimed at both the toxins and the spore germination would be a good addition.

The antibodies may be polyclonal antibodies obtained by immunizing a suitable animal with the spores derived from strains used for preparing the compositions according to the invention, under conventional conditions for preparing such antibodies.

The antibodies may be monoclonal antibodies obtained in a way known per se, in particular by fusing spleen cells from mice immunized with an antigen consisting of spores derived from strains used for preparing the compositions according to the invention.

A subject of the present invention is also purified antigenic preparations, characterized in that they are derived from *B. anthracis* spores and comprise, for example, one or more of the exoantigens (proteins of spores and of the exosporium) of respective molecular weights 15 kDa, 30 kDa, 55 kDa, and greater than 200 kDa, said molecular weights being determined using the AMERSHAM® LMW Electrophoresis Calibration Kit.

In accordance with the invention, the antigenic compositions are obtained by conventional techniques known to those skilled in the art.

The subject of the present invention is also the polyclonal or monoclonal antibodies directed against said antigen compositions.

The immunogenic and vaccine compositions according to the invention may be administered alone or in combination with other vaccines, by injection or by any route conventionally used for vaccination.

The doses to be administered will be determined depending on the animal or the person for whom protection is being sought.

Other characteristics and advantages of the invention appear in the remainder of the description and examples illustrated by the figures in which:

FIG. 1 represents the immunoblot analysis of the spore proteins according to the procedure described in example 5, FIGS. 2A and 2B represent the immunoblot analysis of the exosporium proteins (A) revelation with a polyclonal antibody and a monoclonal antibody (35B8) (B) analysis according to the procedure described in example 5, FIG. 3 represents the various strains of *B. anthracis* used to prepare the RPLC2 strain. The RPLC2 strain produces the toxin components inactivated by point mutations in the active sites of the LF (LF686; H686→a) and EF (EF346/353; K346→Q and K353→Q) protein. In this figure, the numbers which follow Δ indicate the nucleotides at which the deletions begin and end; Erm, Kan and Sps indicate the insertion of erythromycin resistance, kanamycin resistance and spectinomycin resistance cassettes; Ø corresponds to an organism which has no resistance to these antibiotics.

EXAMPLE 1

Materials and Methods for Preparing the Compositions According to the Invention 1.1. Construction of the RPLC2 Strain The RPCL2 strain (Collection Nationale de Cultures et de Microorganismes held by the Institut Pasteur under the number I-2270, dated Jul. 28, 1999) is constructed from the strains indicated in FIG. 3, according to the operating principles described by C. Pezard et al. (1993) (reference cited).

1.2 Preparation of PA

The PA protein is prepared from the mutant *B. anthracis* strain RP42 (Collection Nationale de Cultures et de Microorganismes [National Collection of Cultures and of Microorganisms] held by the Institut Pasteur under the number I-2271, dated Jul. 28, 1999).

The medium R culture supernatants (Ristroph J. D. et al. (1983) *Infection and Immunity,* 39, 483–486) are filtered and then concentrated on a Minitan® system (Millipore® PLGC OMP membrane).

The PA antigen is then purified by ultra-rapid chromatography (FPLC) on a monoQ® column according to the protocol described by Pezard C. et al. (1993) (reference cited).

1.3. Preparation and Inactivation of Spores

The spores are prepared from the Sterne 7702 strain according to the procedure described by E. Guidi-Rontani et al. (1999) (reference cited).

The spores are prepared on a solid NBY medium and then washed with distilled water. They are inactivated by treatment with formol, at a final concentration of 4%, for 3 hours at 37° C.

After washing by centrifugation, the spores are taken up in the initial volume of physiological saline (final concentration of $10^9$ spores/ml).

This suspension is used to perform the immunization.

If necessary, in particular when the intention is to prepare a vaccine for human use, the spores may be purified before the formol treatment, on a 50% to 76% gradient of Radioselectran® (Schering S.A.).

1.4 Preparation of the Vaccine Compositions

The compositions are prepared either from killed spores alone, prepared according to the procedure described in 1.3, or from a mixture of PA (at a concentration such that 10 μg per mouse are injected) and of killed spores ($10^8$ spores per mouse), to which either aluminum hydroxide at a final concentration of 0.3% or saponin at a final concentration of 0.05% is added as an adjuvant.

1.5 Protocol for Treating Mice

Six-week-old female Swiss mice supplied by the company Iffa-Credo (BP0102–69592 L'ARBRESLE-Cedex) are used.

The animals are divided up into groups of six and fed ad libitum.

The injections are given subcutaneously into the groin, in a volume of 200 μl.

1.6. Titering Antibody Levels

The antibody levels are titered using a conventional ELISA assay.

EXAMPLE 2

Effect of Two Immunizations Under the Conditions for the Human Acellular Vaccine (Protocol No. 1)

2.1. Treatment of Animals

The injection protocol for each group is as follows:

- two injections of vaccine compositions prepared as indicated in point 1.4. or of adjuvant (aluminum hydroxide) are given 28 days apart and
- a challenge injection is given on the 43rd day, with the virulent *B. anthracis* strain 17JB (Pasteur reference strain No. 2) provided by the company Rhône-Mérieux.

Four groups of animals are immunized according to this protocol as follows:

- the first group receives the aluminum hydroxide alone (control group),
- the second group receives a PA dose of 10 μg per mouse,
- the third group receives the spores alone, at $10^8$ spores per mouse, and
- the fourth group receives the PA+killed spores mixture so as to have 10 μg of PA and $10^8$ spores per mouse.

All the groups receive, on the 43rd day, as specified above, a challenge dose corresponding to 30 times the LD50, i.e. $1.5 \times 10^4$ spores per mouse.

2.2. Results

The survival rates are given in table I below.

TABLE I

| Treatment | Number of deaths at the 43rd day | Percentage survival at the 43rd day |
|---|---|---|
| Adjuvant alone | 6/6 | 0% |
| PA alone | 3/6 | 50% |
| Killed spores alone | 2/6 | 33% |
| PA + killed spores | 0/6 | 100% |

These results clearly show that only the vaccine compositions according to the invention are capable of allowing complete protection.

EXAMPLE 3

Effect of Two Immunizations Under the Conditions for the Vaccine for Human use (Protocol No. 2)

3.1. Treatment of Animals

The injection protocol for each group is as follows:

two injection of vaccine compositions prepared as indicated in point 1.4. or of adjuvant (aluminum hydroxide) are given 21 days apart, and a challenge injection is given on the 32nd day, with the virulent *B. anthracis* strain 17JB (Pasteur reference strain No. 2) provided by the company Rhône-Mérieux.

Four groups of animals are immunized according to this protocol as follows:

the first group receives the aluminum hydroxide alone, the second group receives a PA dose of 10 μg per mouse, the third group receives the spores alone, at $10^8$ spores per mouse, and the fourth group receives the PA+killed spores mixture so as to have 10 μg of PA and $10^8$ spores per mouse.

All the groups receive, on the 32nd day, as specified above, a challenge dose corresponding to 100 times the LD50, i.e. $1.5\times10^4$ spores per mouse.

3.2. Results 3.2.1. Survival Rates

The results are given in table II below

TABLE II

| Treatment | Number of deaths at the 32nd day | Percentage survival at the 32nd day |
|---|---|---|
| Adjuvant alone | 6/6 | 0% |
| PA alone | 1/6 | 83% |
| Killed spores alone | 1/7 | 85% |
| PA + killed spores | 0/6 | 100% |

These results clearly show that only the vaccine compositions according to the invention are capable of allowing complete protection.

3.2.2. Antibody Levels

The levels of antibodies directed against the spores are high, of the order of 10 000 to 15 000, and identical in the two groups which received them, whether these spores are alone or combined with PA.

These results confirm the synergistic effect of the compositions according to the invention, which, with an antibody level identical to that obtained by injecting the killed spores alone, allows complete protection.

EXAMPLE 4

Comparison of the Efficacy of the Vaccine Compositions According to the Invention with the Sterne Live Vaccine, Under the Conditions for the Vaccine for Veterinary Use (a Single Injection Using Saponin as the Adjuvant): Challenge with the 17JB Strain 4.1. Treatment of Animals The injection protocol for each group is as follows:

one injection of vaccine composition prepared as indicated in point 1.4. or of saponin is given on D0, and a challenge injection is given on the 32nd day, with the virulent *B. anthracis* strain 17JB (Pasteur reference No. 2) provided by the company Rhône-Mérieux.

Five groups of animals are immunized according to this protocol as follows:

the first group receives saponin alone (control group), the second group receives a PA dose of 10 μg per mouse, the third group receives the spores alone, at $10^8$ spores per mouse, the fourth group receives the PA+killed spores mixture so as to have 10 μg of —PA and $10^8$ spores per mouse, and the fifth group receives the Sterne live vaccine prepared at the Institut Pasteur.

All the groups receive a challenge dose corresponding to 100 times the LD50, i.e. $10^5$ spores, on the 32nd day.

4.2. Results

They are given in Table III below.

TABLE III

| Treatment | Number of deaths at the 32nd day | Percentage survival at the 32nd day |
|---|---|---|
| Adjuvant alone | 6/6 | 0% |
| PA alone | 1/6 | 83% |
| Live spores | 0/6 | 100% |
| Killed spores alone | 4/6 | 33% |
| PA + killed spores | 0/6 | 100% |

These results clearly show that the vaccine compositions according to the invention are as efficacious as the live vaccine and may, consequently, advantageously be used as a veterinary vaccine.

EXAMPLE 5

Immunoblot Analysis of the *B. anthracis* Spore Proteins 5.1. Materials and Methods 5.1.1. Preparation of the Polyclonal and Monoclonal Antibodies A polyclonal serum from mice immunized with killed spores derived, for example, from the RPLC2 strain (Collection Nationale de Cultures et de Microorganismes [National Collection of Cultures and of Microorganisms] held by the Institut Pasteur under the number I-2270, dated Jul. 28, 1999) is prepared according to conventional techniques known to those skilled in the art.

The monoclonal antibody specific for the spore surface (35B8) is prepared according to the technique described by Kohler et al. (1975), *Nature,* 296, 495–497.

5.1.2. Extraction of the Spores

The proteins from the spore are solubilized by treating the spores with a Tris-HCl buffer, at pH 9.8, containing 8M of urea and 2% of SDS, or with a 10 mM Tris buffer at pH 9.5, containing 10 mM of EDTA and 1% of SDS, according to the technique described by Garcia-Patrone (1995), *Molecular and Cellular Biochem.,* 145, 29–37).

5.2. Results

Figure 2:
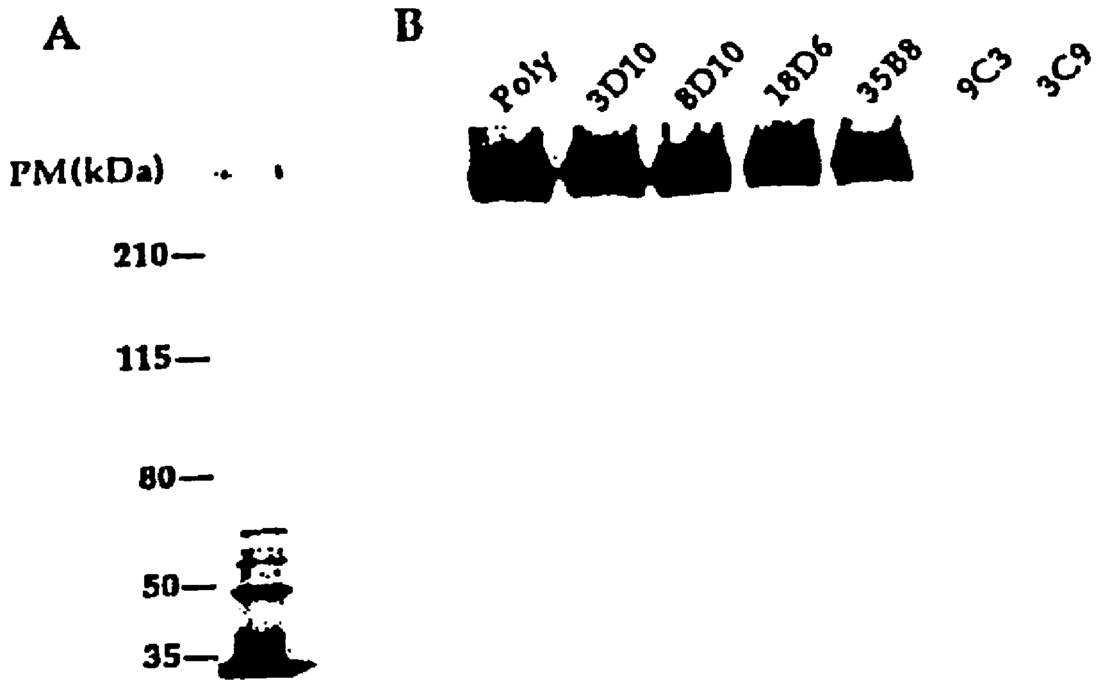

They are illustrated in FIG. 1 and FIG. 2.

The mouse polyclonal serum recognizes 3 protein species of respective molecular weights 15 kDa, 30 kDa, 55 kDa and a protein species of molecular weight greater than 200 kDa (FIG. 1).

The heaviest species is also recognized by the monoclonal antibody 35B8 and appears to belong to the exosporium (FIG. 2A).

Specifically, the immunoblot analysis of the exosporium proteins shows that the various monoclonal antibodies used, including 35B8, recognize a protein species of molecular weight greater than 200 kDa (FIG. 2A).

It emerges from the above that the vaccine compositions according to the invention are capable of allowing complete protection both under the conditions for the human vaccine and under the conditions for the veterinary vaccine.

EXAMPLE 6

Comparison of the Efficacy of the Vaccine Compositions According to the Invention Administered According to Protocol No. 1 of Example 2, with the PA Antigen Alone, in Mice or in Guinea Pigs: Challenge with the 9602 Strain A. Swiss Mice 6.1 Treatment of Animals The injection protocol for each group is as follows:

- two injections of the vaccine compositions prepared as indicated in point 1.4 in example 1 are given 15 days apart (D0 and D15), and
- a challenge injection is given on the 35th day, with the virulent strain 9602 (M. Berthier et al., Lancet, 1996, 347, 9004:828) isolated from a lethal case of human anthrax, and the virulence of which is ten times greater than that of the 17JB strain used in the previous examples; said strain is injected subcutaneously.

4 groups of animals as defined in example 2 are immunized according to this protocol.

All the groups receive, on the 35th day, as specified above, a challenge dose corresponding to 30 times the LD50, i.e. $1.5\times10^4$ spores per mouse.

6.2. Results

The experiments were repeated 3 times, with different preparations, on batches of 6 to 8 mice per point (due to P3 containment).

The survival rates are illustrated in table IV below.

TABLE IV

| Treatment | Percentage survival at the 35th day and up to the 43rd day |
|---|---|
| Adjuvant alone | 0% |
| PA alone | 0% |
| Killed spores alone | 0% |
| PA + killed spores | 100% |

B. Guinea Pigs

The experiments were carried out twice, on batches of 5 guinea pigs. The protocol is similar to that used in the mice, with the exception of the following points:

- the PA doses are 40 μg per animal,
- the challenge injection is given intramuscularly.

100% survival is obtained for the combination according to the invention, which is killed spores+PA versus 40% in the animals receiving PA alone, which is the composition of the conventional vaccine.

6.3. Antibody Levels

These experiments (mice and guinea pigs) were accompanied by monitoring of the antibody response by ELISA on serum samples from mice and from guinea pigs. The anti-PA antibody titers are high (>5 000); a response of the same order is detected against spore-specific antigens.

EXAMPLE 7

Comparison of the Efficacy of the Vaccine Compositions According to the Invention with the Sterne Live Vaccine, Under the Conditions for the Vaccine for Veterinary Use as Described in Example 4 (Challenge with the 9602 Strain)

The test was carried out on Swiss mice (under the conditions described in example 4). The challenge injection is given with the 9602 strain (M. Berthier et al., mentioned above), to mice which have received a single injection either of live spores (RPLC2) or of the combination according to the invention, which is killed spores+PA. The protection efficacy, 83%, is identical for both batches.

These results clearly show that it is possible to provide 100% protection of mice and guinea pigs with a vaccine combination comprising killed spores and the PA antigen.

What is claimed is:

1. An acellular immunogenic composition capable of inducing an immune response against *B. anthracis* infections, comprising:

an isolated protective anthrax antigen from *B. anthracis,* killed and purified spores obtained from a mutant strain of *B. anthracis* lacking pXO2 plasmids, and a pharmaceutically acceptable vehicle.

2. The acellular immunogenic composition as claimed in claim 1, which induces the production of antibodies against *B. anthracis.*

3. The acellular immunogenic composition as claimed in claim 1, which further comprises at least one detoxified exotoxin selected from the group consisting of a lethal factor and a edematogenic factor.

4. The acellular immunogenic composition as claimed in claim 1, wherein the spores are isolated from a strain of *B. anthracis* selected from the group consisting of the following strains: Sterne 7702, RPLC2 (Collection Nationale de Cultures et de Microorganismes (National Collection of Cultures and of Microorganisms) held by the Institute Pasteur under the number I-2270, dated Jul. 28, 1999) and RP42 (Collection Nationale de Cultures et de Microorganismes (National Collection of Cultures and of Microorganisms) held by the Institute Pasteur under the number I-2271, dated Jul. 28, 1999).

5. The immunogenic composition as claimed in claim 1, wherein the isolated protective anthrax antigen is selected from the group consisting of purified protective antigens isolated from a wild-type or mutated Sterne strain of *B. anthracis* and a recombinantly produced protective antigen of *B. anthracis.*

6. The immunogenic composition or vaccine composition as claimed in claim 1, wherein the isolated protective anthrax antigen is isolated from the RP42 strain (Collection Nationale de Cultures et de Microorganismes (National Collection of Cultures and of Microorganism) held by the Institute Pasteur under the number I-2271, dated Jul. 28, 1999).

7. An acellular vaccine composition against *B. anthracis*, comprising:

an isolated protective antigen from *B. anthracis*, and killed and purified spores obtained from a mutant strain of *B. anthracis* lacking pXO2 plasmids, a pharmaceutically acceptable vehicle, and at least one adjuvant.

8. The vaccine composition of claim 7, which further comprises at least one detoxified exotoxin selected from the group consisting of a lethal factor and an edematogenic factor.

9. The vaccine composition of claim 7, wherein the spores are isolated from a strain of *B. anthracis* selected from the group consisting of the following strains: Sterne 7702, RPLC2 (Collection Nationale de Cultures et de Microorganismes (National Collection of Cultures and of Microorganisms) held by the Institute Pasteur under the number I-2270, dated Jul. 28, 1999) and RP42 (Collection Nationale de Cultures et de Microorganismes (National Collection of Cultures and of Microorganisms) held by the Institute Pasteur under the number I-2271, dated Jul. 28, 1999).

10. The vaccine composition of claim 7, wherein the isolated protective antigen is selected from the group consisting of purified protective antigens isolated from a wild-type or mutated Sterne strain of *B. anthracis* and a recombinantly produced protective antigen of *B. anthracis*.

11. The vaccine composition of claim 7, wherein the protective antigen is isolated from the RP42 strain (Collection Nationale de Cultures et de Microorganismes (National Collection of Cultures and of Microorganism) held by the Institute Pasteur under the number I-2271, dated Jul. 28, 1999).

12. The acellular immunogenic composition as claimed in claim 1, which contains killed and purified spores obtained from a mutant strain of *B. anthracis* lacking pXO2 plasmids and having pXO1 plasmids.

13. The acellular vaccine composition as claimed in claim 7, wherein the spores are obtained from *B. anthracis* lacking pXO2 plasmids and having pXO1 plasmids.

* * * * *